(12) United States Patent
Binder

(10) Patent No.: US 8,883,143 B2
(45) Date of Patent: *Nov. 11, 2014

(54) TREATMENT OF TRAUMATIC-INDUCED MIGRAINE HEADACHE

(71) Applicant: Miotox, LLC, Beverly Hills, CA (US)

(72) Inventor: William J. Binder, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/986,197

(22) Filed: Apr. 10, 2013

(65) Prior Publication Data

US 2013/0315890 A1 Nov. 28, 2013

Related U.S. Application Data

(63) Continuation of application No. 13/478,828, filed on May 23, 2012, now Pat. No. 8,420,106.

(51) Int. Cl.
*A61K 38/16* (2006.01)
*A61K 38/48* (2006.01)

(52) U.S. Cl.
CPC ............... *A61K 38/164* (2013.01); *A61K 38/48* (2013.01)
USPC ...................................... 424/94.63; 514/17.7

(58) Field of Classification Search
CPC ..... A61K 38/164; A61K 38/48; A61K 39/08; A61K 38/4893; C07K 14/00; C07K 14/33; C07K 16/1282; G01N 2333/33

USPC ................................. 424/94.63, 9.1; 514/17.7
See application file for complete search history.

(56) References Cited

U.S. PATENT DOCUMENTS 8,420,106 B1 * 4/2013 Binder ........................ 424/239.1

* cited by examiner

*Primary Examiner* — Chih-Min Kam

(57) ABSTRACT

A method for selection and treatment of externally caused migraine headache, the method includes identifying a patient group having chronic migraine headache; determining the identified patient group, a specific patient with a post traumatic migraine headache; and administering to the selected patient by injection of a therapeutically effective amount of an invertebrate presynaptic neurotoxin in a pharmaceutically safe form to the selected patient's head or upper neck; administration preferably being on the sites of the trigeminal cervical system, enabling axonal transport of the neurotoxin from distal to central sites; and the administration preferably comprising extramuscular injection of the neurotoxin of suitable dilution (a) over the aponeurotic fascia to enable the neurotoxin to diffuse into distal sensory nerves, in order to concentrate the neurotoxin over the occipital-parietal-frontal head region, or (b) intra-orally, in a foramina of the sphenopalatine ganglion for enabling diffusion of the neurotoxin to the ganglion, or (c) to emerging exit points of nerves including foraminal sites for enabling the neurotoxin access to concentrated nerve bundles at exit points of the foramina.

8 Claims, 2 Drawing Sheets

TREATMENT OF TRAUMATIC-INDUCED MIGRAINE HEADACHE

The present patent application is a continuation of U.S. patent application Ser. No. 13/478,828, which was filed on May 23, 2012 in the name of William J. Binder.

Trauma has been documented to increase frequency of migraine headache and is a risk factor for conversion from episodic to chronic migraine.

Anxiety and depression are more often associated with chronic migraine than episodic migraine, while trauma may be implicated in initiating or worsening migraine. There are a number of different trauma modalities that can be involved in this process such as:
1. Closed head injury, this includes blast injuries
2. Open head injury, with intra-parenchymal lesions such as hematomas and contusions
3. Post craniotomy with trauma secondary to surgical effects as well as the underlying condition
4. Psychological trauma, such as depression, anxiety, post traumatic syndrome and post-traumatic stress disorder (PTSD)
5. Whiplash injury as well as other soft tissue injuries around the head and neck area The International Headache Society classifies post-traumatic headache and migraine separately. The post-traumatic headache requires that the headache start within one week of the trauma. If the headache persists for less than 3 months after this it is referred to as an Acute Post-Traumatic headache. If the headache persists for longer than 3 months it is referred to as a Chronic Post-Traumatic headache. These headaches are further sub-divided into mild, moderate or severe depending on the extent of the injury that caused the headache. In addition there is a category for headaches attributed to whiplash injury. The actual features of the post-traumatic headache are not described in the classification but these can resemble migraine features. Furthermore episodic migraine can transform to chronic migraine as a result of head trauma. In these cases there is a prior history of migraine, which increases in frequency after the trauma.

Botulinum toxins have been used to treat migraine headache. This is well established in the art. By way of example only, see U.S. Pat. No. 5,714,468, U.S. Pat. No. 5,721,215, U.S. Pat. No. 6,458,365, U.S. Pat. No. 7,655,244, U.S. Pat. No. 7,704,511, and U.S. Pat. No. 7,981,433. All of these references are to be incorporated herewith in their entirety. These patents include: Binder; Botulinum toxin injections to the head for migraine, Blumenfeld; Botulinum toxin injections to the sphenopalatine ganglion, nasal approach and vascular approach, suture line technique (these are not foramina or exit points); Aoki; Tension type headache treatment with Botulinum toxin, and Turkel; 31 sites as for the FDA approved protocol for chronic migraine.

Heretofore, onabotulinumtoxinA has been FDA approved for chronic migraine, and the dose used is 155 to 195 units, with a dilution of 2 cc per 100 units of onabotulinumtoxinA. Doses ranging from 25 units to 260 units have been used to treat various headache disorders. These have involved intramuscular injections in fixed sites and follow the pain sites.

Botulinum toxin side effects are usually due to local diffusion to surrounding muscles producing unwanted weakness.

SUMMARY OF THE INVENTION

The method in accordance with the present invention for selection and treatment of externally caused migraine headache generally includes identifying a patient group having migraine headache, and of the identified patient group, determining a specific patient with a post traumatic migraine headache. Thereafter, the selected patient is administered with a therapeutically effective amount of an invertebrate presynaptic neurotoxin in a pharmaceutically safe form to the selected patient's head.

The present invention is also directed to treating post-traumatic migraine headaches with Botulinum toxin (and/or endopeptidase) by adjusting the toxin concentration and volume to establish optimum diffusion of toxin in non-muscle related areas of the head and neck, such as fascia injections to the scalp or exit points of nerves in the mouth and neck. The improvement avoids side effects such as muscle paralysis and reduces doses overall, e.g., use of high concentration/low volume injections at nerve exit points and low concentration/high volume injections in fascia on the scalp.

The present invention includes but is not limited to closed head injury, including blast injuries; open head injury, with intra-parenchymal lesions such as hematomas and contusions, post craniotomy with trauma secondary to surgical effects; psychological trauma, such as depression, anxiety, and post-traumatic stress disorder; and whiplash injury as well as other soft tissue injuries around the head and neck area The preferred method in accordance with the present invention for selection and treatment of externally caused migraine headache generally includes identifying a patient group having migraine headache, and of the identified patient group, determining a specific patient with a post traumatic migraine headache. Thereafter, the selected patient is administered with a therapeutically effective amount of an invertebrate presynaptic neurotoxin in a pharmaceutically safe form to non-muscle related areas of the selected patient's head and neck. In many of these selected post-traumatic headache patients, unwanted side effects of muscle weakness associated with the use of Botulinum toxins cannot be tolerated.

In general, a method for treating a patient with migraine headache in accordance with the present invention includes administering to the patient a therapeutically effective amount of an invertebrate presynaptic neurotoxin in a pharmaceutically safe form.

The administration advantageously includes extramuscular injection of the neurotoxin of suitable dilution (a) over the aponeurotic fascia to enable the neurotoxin to diffuse into distal sensory nerves, in order to concentrate the neurotoxin over the occipital-parietal-frontal head region, or (b) intraorally, in a foramina of the sphenopalatine ganglion for enabling diffusion of the neurotoxin to the ganglion, or (c) to emerging exit points of nerves including foraminal sites for enabling more concentrated dilution of the neurotoxin access to concentrated nerve bundles at exit points of the foramina.

The invention further includes the following methods:

The method wherein the neurotoxin is delivered to the face, cranium, and neck.

The method wherein externally caused migraine headache is post-traumatic stress disorder (PTSD).

The method wherein externally caused migraine headache is traumatic brain injury (TBI).

The method wherein the presynaptic neurotoxin is a Botulinum toxin.

The method where the Botulinum toxin is Botulinum toxin A.

The method wherein the neurotoxin comprises an Endotoxin.

The method wherein the Endotoxin is an endopeptidase derived from botulinum toxin.

In general, the present invention aims to minimize the side effects present with prior injection techniques and uses a novel injection approach to achieve this goal. In addition, this invention aims to increase the efficacy across multiple headache types including chronic and episodic migraine, post-traumatic headache, post-craniotomy headache, tension type headache and medication overuse headache. This invention focuses the medication on the sites of maximal benefit; i.e., the trigemino-cervical nerves and the sphenopalatine ganglion nerves.

The technique involves administration to allow for maximizing the dose and thus the effect on the trigeminal cervical system and sphenopalatine ganglion system; while minimizing the side effects.

This invention uses the same methods of administration described in the procedures above to deliver endotoxins to the same sites. Endotoxins do not cause muscle weakness as they are targeted to sensory nerves, however the current technique of intra-muscular injections can still cause side effects related to needle trauma to muscle and the need to perform multiple injections.

More specifically, the administration includes the extra-muscular injection of diluted Botulinum toxin.

Still more particularly, the method the Botulinum toxins may be Botulinum Toxin A, B, C, D, E, F, and G.

BRIEF DESCRIPTION OF THE DRAWINGS

The advantages and features of the present invention will be better understood by the following description when considered in conjunction with the accompanying drawings, in which.

DETAILED DESCRIPTION

Figure 1:
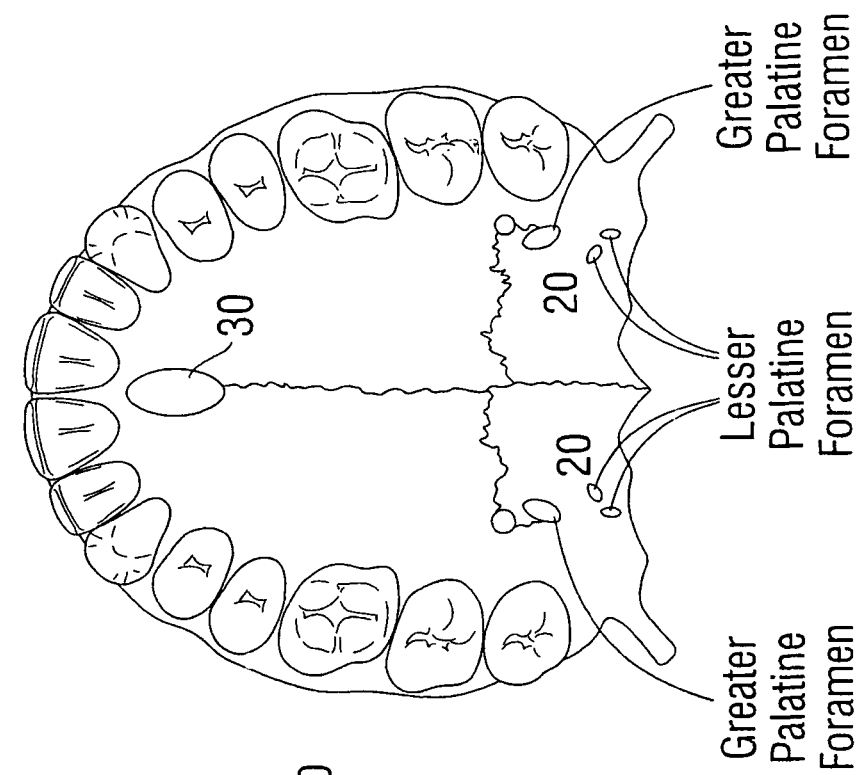
FIG. 1 is a diagram of injection sites in accordance with the present invention showing the frontal (10), parietal (20), and occipital (30) aponeurotic fascia in head 14.

It has been reported that nearly forty-percent (40%) of soldiers had migraines or probable migraines during their tours of duty, but few had a history of migraines before their deployments. In accordance with the present invention, a patient group can be identified by survey. For example, nineteen percent (19%) of the 2,687 soldiers surveyed upon return from duty met the criteria for definite migraines, eighteen percent (18%) had probable migraines, and eleven percent (11%) non-migraine-type headaches. Those with definite migraines had an average of 3.5 migraine days/month.

Just five percent (5%) of the soldiers had a history of migraine headaches prior to their deployments to Iraq.

As an example, after returning home from Iraq, soldiers are sent through a medical processing site. Members of one brigade completed a validated 17-question survey about headaches. Based on their survey responses, soldiers were divided into three groups: definite migraines, probable migraines, or non-migraine headaches, a system of classification similar to that used in the American Migraine Study.

The mean age of respondents was 27. The group was ninety-five percent (95%) male and five-percent (5%) female.

Soldiers rated their migraine headaches as a mean 6.5 on a 10-point severity scale, lasting an average of 5.2 hours. Yet only 2% received triptans, the standard of care for the treatment of acute migraines.

Findings from a 3-month follow-up survey indicate that many soldiers continue to have elevated rates of migraines after their return stateside.

After identification of an identified patient group, continued survey can be used to determine specific patients with post-traumatic migraine headache and thereafter the selected patient is administered a therapeutically effective amount of an invertebrate presynaptic neurotoxin in a pharmaceutically safe form specifically to non-muscle related areas of the patients head.

Current injection techniques known in the art today use a system of flooding the potential structures involved with migraine pathogenesis with the medication, but this may lead to unwanted side effects. This invention avoids this by with the most efficiency by targeting the sites of most benefit, i.e., see FIGS. 1-3, with the most efficiency. The technique also utilizes adjustments in concentrations to establish diffusion of medication in non-muscle related areas. Unlike the Blumenfeld patent for the use of Botulinum toxin to treat migraine with a spenopalatine ganglion approach, this invention uses a much more superficial and less painful approach to reach this target than the intra-nasal technique recommended in that patent.

Importantly, the present invention utilizes the proximal axonal transport of Botulinum toxins from distal to central sites.

The technique, in accordance with the present invention involves 3 different modalities of administration to allow for maximizing the dose and thus the effect on the trigeminal cervical system and sphenopalatine ganglion system; while minimizing the side effects.

Injection Modalities:

1. Dilute Botulinum toxin: about 4-10 cc per 100 units is injected over the aponeurotic fascia, not into muscle, allowing the toxin to diffuse into distal sensory nerve endings that are concentrated over the occipital-parietal-frontal head regions. (There is no muscle in this location). No muscle weakness results as all the injections are in non-muscular regions. The toxin diffuses in a broad area due to the dilution; allowing for a decrease in the number of injection sites. Botulinum toxin is delivered to the distal sensory nerve ending in the scalp. See FIG. 1.

2. Intra-oral injections are done in the region of the foramina of the sphenopalatine ganglion, this allows diffusion of toxin to the ganglion without a deep injection through muscle. Thus, lower doses can be used. There is no risk of muscle trauma including intra-muscular hemorrhage related to needles tracking through muscle to reach the sphenopalatine ganglion. The dilution for these injections is about 1 cc per 100 units of Botulinum toxin, to prevent diffusion to other intraoral structures. See FIG. 2.

3. Emerging nerve points which include foraminal injection sites and foraminal injection sites deep to the muscle layer allows Botulinum toxin access to the concentrated nerve bundles at the exit points and thus lower doses with improved efficacy and less side effects and adverse events can be achieved. The cervical plexus emerges from the posterior portion of the sternomastoid muscle and injections at this site can encompass the entire distribution of the cervical plexus. The dilution for these injections is about 1 cc per 100 units of Botulinum toxin. The concentrated solution prevents diffusion to local muscle and the accurate needle placement allows the medication to be delivered to the site where it will most effective. See FIG. 3.

Figure 3:
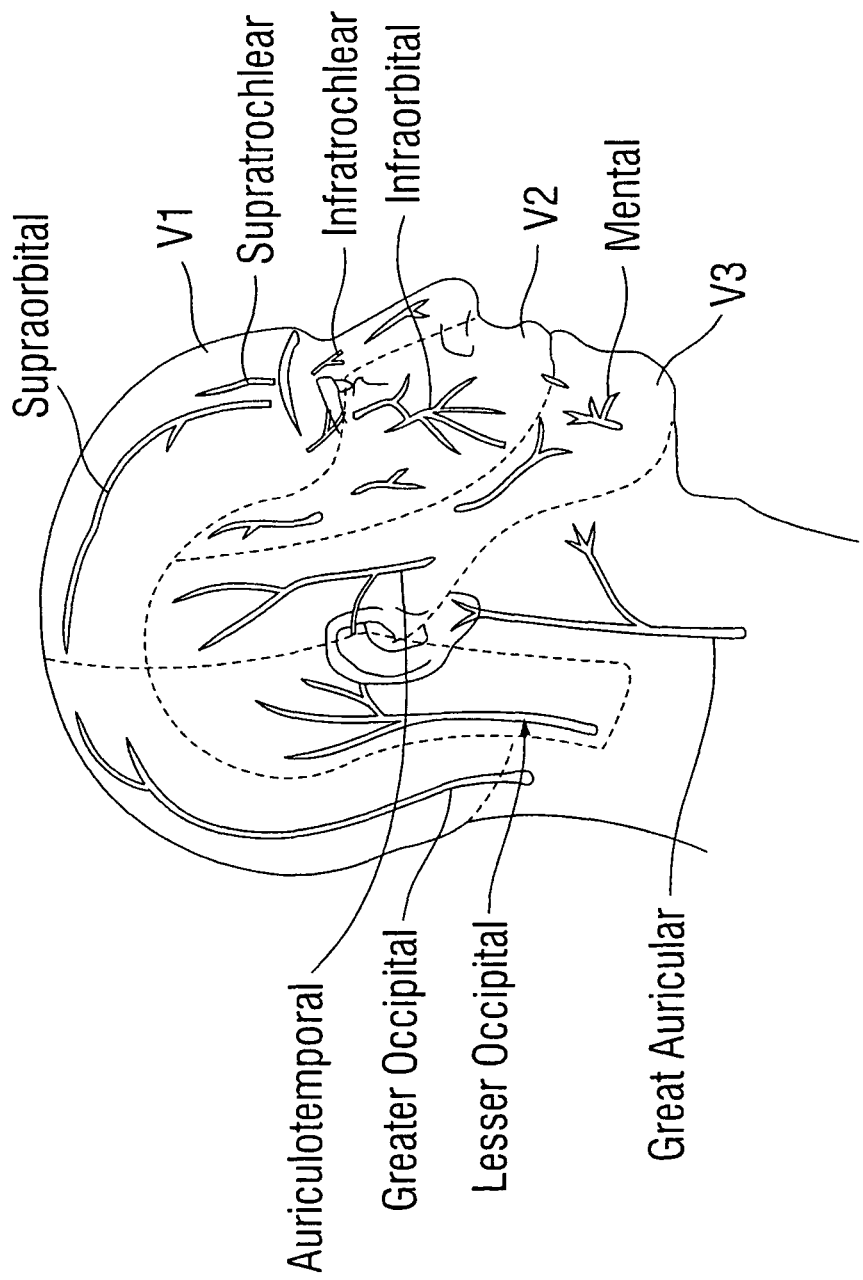
FIG. 3 illustrates suitable nerve exit points in the head and neck.

With reference to FIG. 3, sensory branches of the trigeminal-nerves (ophthalmic V1, maxillary V2 and mandibular V3)

leave the skull through three separate foramina; in the following order: the superior orbital fissure, the foramen rotundum, and the foramen ovale.

V1 carries information from the scalp (forehead to vertex) upper eyelid and eye, nose and nasal mucosa, meninges and frontal sinuses.

V2 carries information from lower eyelid, cheek, upper lip, dentition, mouth meninges and sinuses (ethmoid and sphenoid).

V3 carries information from lower lip, dentition, jaw, external ear, meninges.

Note all 3 divisions supply the meninges.

Figure 2:
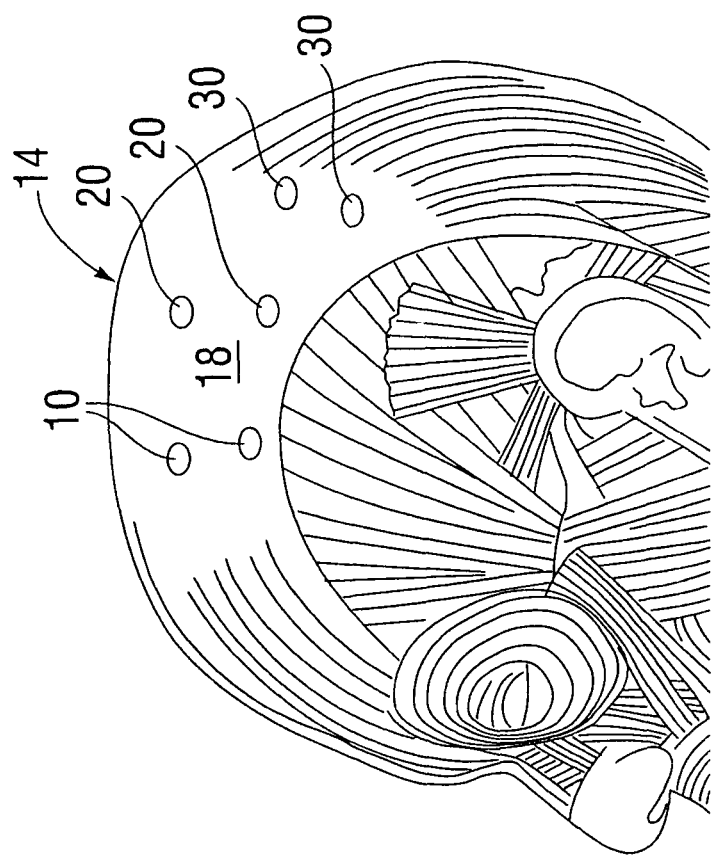
FIG. 2 is a diagram of injection sites in accordance with the present invention; and refers specifically tot eh greater and lesser palatine foramen (20) which are nerve exit points for the palatine nerve and the incisive foramen (30) a nerve exit point for the nasopalatine nerve.

By way of illustration, injections are made at sites 10 on a scalp 14 on each side of the aponeurotic fascia 18 with a 4-10 cc dilution allowing for a broad diffusion of the Botulinum toxin, see FIG. 1. However, for the forminal and emerging nerve bundle injections a 1 cc dilution is used to prevent diffusion to surrounding muscles, see FIGS. 2 and 3.

The foraminal anatomy is as follows:
Frontal region—supraorbital foramen—supra-orbital nerve
Supratrochlear foramen—supratrochlear nerve
Maxilla—incisive foramen—nasopalatine nerve (Septum)
Palatine—greater and lesser palatine foramen—greater and lesser palatine nerves
Maxilla—Inferior orbital fissure/foramen—zygomatic and infra-orbital nerves and orbital branch of the pterygopalatine ganglion (SPG).

There are two possible intra-oral approaches to the Sphenopalatine ganglion. See FIG. 2. The first intra-oral method involves needle insertion in the region of the mucobuccal fold (not shown) at the maxillary second molar and advancing the needle in a posterior, superior, and medical direction, into the region of the pterygopalatine fossa. The second intra-oral approach to the Sphenopalatine ganglion 20 is through the greater palatine canal. The opening of this is located between the middle of the second molar and the middle of the third molar. This site will be approximately 7 mm from the end of the hard palate.

Clinical Examples

Case 1

18 year old male returns from Iraq where he sustains a blast closed head injury and since that time has daily headaches that have features suggestive of migraine headache. He fails to respond to tricyclic antidepressants and biofeedback courses. Onabotulinum toxin is injected using the FDA approved protocol for onabotuliumtoxinA. He tolerates the procedure well. He has no side effects. After 10 weeks he reports no further headaches.

Case 2

22 year old male returns from Iraq where he sustains a blast closed head injury and since that time has daily headaches that have features suggestive of migraine headache. He fails to respond to tricyclic antidepressants and biofeedback courses. He meets criteria for chronic migraine complicated by medication overuse headache. He also fails to respond to numerous preventive medications such as Topiramate and Propranolol. He is treated with onabotulinumtoxinA using the PREEMPT injection protocol with fixed sites and follow-the-pain injections. Total dose given 195 units. He develops neck pain, brow ptosis and shows no improvement in headache frequency after three (3) treatment cycles.

He is then treated with the variable concentration focused injection protocol as outlined in this invention.

OnabotulinumtoxinA is diluted as follows: 100 units in 8 cc of normal saline (0.1 ml contains 1.25 units) and 100 units in 1 cc of normal saline (0.1 ml contains 10 units).

Injection sites and dosing as Follows:
8 cc Dilution
Frontal aponeurotic fascia 5 units each side
Parietal aponeuotic fascia 5 units each side
Occipital-aponeurotic 5 units each side
Sub-total 30 units
1 cc Dilution
Orbital ridge supro-medial angle over supra-trochlear and supra-orbital nerves 5 units each side
Infraorbital foramen 5 units each side
Mental foramen 5 units each side
Posterior aspect, mid-section of sternocleidomastoid muscle 5 units each side
Occipital foramen 5 units each side
Auriculotemporal nerve just anterior and inferior to-the tragus 5 units each side
Intra-oral muscosal injection superior to second molar intra-oral 5 units each side
Sub-total 60 units
Total dose given 100 units.

Lower dosing of onabotulinumtoxinA is used as the medication is delivered in a focus where it will have the most benefit; i.e.: no unnecessary flooding of medication to unwanted sites. 20 injections are done instead of the more conventional 39. None of these sites match the approved PREEMPT injection protocol for migraine. He tolerates the procedure well. He has no side effects. The patient does not develop neck weakness or pain as the neck musculature is not injected. The patient does not develop brow ptosis as the frontalis muscle is not injected. After 10 weeks he reports no further headaches.

Case 3

19 year old male, returns from Iraq with a history of migraine headaches present on 4 days out of each week. He was in Iraq for over a year, but during this time he did not sustain any injuries in particular no head injury. Prior to deployment he did not suffer with headaches. His current headaches are generalized, throbbing in nature, associated with nausea and photo-phobia. They interfere with his ability to work. He is assessed as having chronic migraine triggered by stress relating to his deployment. He is successfully treated with onabotulinumtoxinA in accordance with the injection methodology set forth in Case 1.

Case 4

28 year old woman is involved in a motor vehicle accident with blunt head trauma that results in an acute left epidural hematoma. She undergoes urgent craniotomy. The hematoma is evacuated via a left prieto-temporal craniotomy. She gradually recovers but her course is complicated by ongoing headaches overt the left hemicranium. These are throbbing in nature, interfere with her activities, and associated with nausea and vomiting. These headaches are present on a near daily basis. She is successfully treated treated with onabotulinumtoxinA in accordance with the injection methodology as outlined in case 1 above.

The present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A method for selection and treatment of externally caused migraine headache, said method comprising:
    identifying a patient group having migraine headaches;
    of the identified patient group, determining a specific patient with a post traumatic chronic migraine headache; and
    administering a therapeutically effective amount of an a suitably diluted Botulinum toxin in a pharmaceutically safe form to the selected patient's head to reduce chronic migraine headaches.

2. The method according to claim 1 wherein the externally caused chronic migraine headache is post-traumatic stress disorder (PTSD).

3. The method according to claim 1 wherein the externally caused chronic migraine headache is traumatic brain injury (TBI).

4. The method according to claim 3 wherein the Botulinum toxin is Botulinum toxin A.

5. The method according to claim 4 wherein the Botulium toxin A is onabotulinumtoxinA.

6. The method according to claim 3 wherein the Botulinum toxin is Botulinum Toxin B.

7. The method according to claim 1 wherein the Botulinum toxin is an Endotoxin.

8. The method of claim 7 wherein the Endotoxin is an endopeptidase.

* * * * *

UNITED STATES PATENT AND TRADEMARK OFFICE
CERTIFICATE OF CORRECTION

PATENT NO. : 8,883,143 B2  
APPLICATION NO. : 13/986197  
DATED : November 11, 2014  
INVENTOR(S) : Binder It is certified that error appears in the above-identified patent and that said Letters Patent is hereby corrected as shown below:

On the Title page item [63] and in the Specification, col. 1, lines 5-6, Patent application 13/986,197 also claimed priority to U.S. Provisional Application No. 61/609,817, filed on March 12, 2012. As such, the priority claim should read as follows:

U.S. Patent Application 13/986,197, filed on April 10, 2013 is a continuation that claims priority to 13/478,828, filed on May 23, 2012, now US 8,420,106, that claims priority to U.S. Provisional Application No. 61/609,817, filed on March 12, 2012.

Signed and Sealed this  
Eighth Day of September, 2015

Michelle K. Lee  
*Director of the United States Patent and Trademark Office*